United States Patent [19]

Svenson et al.

[11] Patent Number: 5,172,699
[45] Date of Patent: Dec. 22, 1992

[54] PROCESS OF IDENTIFICATION OF A VENTRICULAR TACHYCARDIA (VT) ACTIVE SITE AND AN ABLATION CATHETER SYSTEM

[75] Inventors: Robert H. Svenson, Charlotte, N.C.; Wendell King, North Oaks, Minn.

[73] Assignee: AngeLase, Inc., Plymouth, Minn.

[21] Appl. No.: 601,249

[22] Filed: Oct. 19, 1990

[51] Int. Cl.$^5$ .............................................. A61B 5/046
[52] U.S. Cl. ...................... 128/705; 606/46; 606/7
[58] Field of Search ................ 128/705; 604/21; 606/732-33, 46, 47

[56] References Cited

U.S. PATENT DOCUMENTS

| | | | |
|---|---|---|---|
| 4,296,755 | 10/1981 | Jupell | 128/705 |
| 4,641,649 | 2/1987 | Walinsky et al. | 606/33 |
| 4,643,186 | 2/1987 | Rosen et al. | 606/33 |
| 5,000,189 | 3/1991 | Throne et al. | 128/705 |
| 5,011,483 | 4/1991 | Sleister | 606/32 |

OTHER PUBLICATIONS

Gillette, Paul C. "Catheter Ablation in Dysrhythmias", Cardio, Mar., 1984, pp. 67-69, copy in 606/032.

Primary Examiner—William E. Kamm
Attorney, Agent, or Firm—Hugh D. Jaeger

[57] ABSTRACT

An electrophysiologically guided arrhythmia ablation system for ventricular tachycardia or other arrhythmia. The system combines a system for recording the electrical activtion time of various parts of the heart for locating an active site of the arrhythmia, with a system for delivering energy for ablation of the arrhythmia. The system has the capability of processing local myocardial electrical activation data and triggering the ablation energy source when at the active site or inhibiting the release of potentially harmful energy when the device is not at an active site. The process includes identification of an active site occurs during the 20-80%, preferably 35-50%, time period of a diastolic interval. The diastolic interval is monitored by appropriate electrical connections between the heart and a monitor. A mapping device also connects to the monitor which maps for indicating an active site. A timing system connects to the monitor, indicates when an active site is located in the 20-80%, preferably 35-50%, of the diastolic interval, and also connects to a laser system for firing the laser system to ablate the active site. Other ablate energies can be utilized including RF, microwave or DC energy.

8 Claims, 1 Drawing Sheet

VT #1

PROCESS OF IDENTIFICATION OF A VENTRICULAR TACHYCARDIA (VT) ACTIVE SITE AND AN ABLATION CATHETER SYSTEM

This patent application relates to co-pending patent application U.S. Ser. No. 07/601,241, filed Oct. 19, 1990, entitled "Process of Identification of an Active Site of Ventricular Tachycardia and for Electrode Attachment of an Endocardial Defibrillator" to the same assignee as the present patent application.

BACKGROUND OF THE INVENTION

1. Definitions

A. VT—Ventricular tachycardia.

B. Active Site—Critical site to deliver ablation energy to cure VT identified by electrical activations. The energy must be delivered to the heart tissue to ablate the heart tissue.

C. Diastolic—That period of time between two QRS complexes of the electrocardiogram.

D. Ablation—The delivery of destructive energy to the cardiac tissues containing the active site.

2. Field of the Invention

The present invention pertains to a medical system, and more particularly, pertains to cardiac electrophysiology, specifically, ablation of cardiac arrhythmias or modification of the electrical properties of the myocardium. The present invention is also a process for identification of a active site, as well as a catheter system for ablation of the active site of the VT.

3. Description of the Prior Art

In existing technology, the recognition of the site of the origin of the arrhythmias and the ablation function are performed separately. For ventricular tachycardia, there has been no consensus of opinion as to what electrical activation time constitutes the "site of origin". Furthermore, the ablation energy source, whether DC current shock, radio frequency, or laser, has to be separately redirected by visual means to the site of suspected origin of the arrhythmia. Arrhythmia ablation is currently performed during open heart surgery or through catheters directed percutaneously through the heart. During the surgical approach, either a hand-held electrical mapping probe or a computerized array of electrodes acquire electrical activation data seeking the site of origin of the arrhythmia. In the percutaneous catheter based approach, a catheter with recording electrodes is positioned in the heart under fluoroscopic guidance.

Following acquisition of electrical activation data, ablation energy is then later delivered by hand-held probes or catheters either in the operating room or in the cardiac catheterizational lab.

In the prior art, the process for identification of the "site of origin" of the arrhythmia was performed with electrical recording procedures designed to map the spread of electrical activation in the heart looking for the site of earliest electrical activation (site of origin). This procedure is carried out by sequentially moving a hand-held electrical recording probe or catheter over the heart and recording the time of arrival of the electrical impulse to that location. This process turned out to be a long and tedious procedure.

Prior art mapping procedures also include a sock multiple electrode array (epicardial), a balloon endocardial electrode array, a single hand-held mapping probe or a multiple electrode catheter (endocardial) inside a chamber of the heart. These procedures require a skilled surgeon and cardiac electrophysiologist.

The prior art mapping procedures are capable of reconstructing the spread of electrical activation in the heart, but do not in themselves identify the "active site" of the arrhythmia, can be time consuming, and are separate functions from the prior art ablation procedures.

The present invention overcomes the disadvantages of the prior art by recognizing a particular window of electrical activation during the diastolic interval of the arrhythmia where ablation energy could be delivered with a high probability for successful cure.

SUMMARY OF THE INVENTION

The general purpose of the present invention is the process for identifying the critical site to deliver therapeutic ablation energy to cardiac arrhythmia. For ventricular tachycardia, the process involved identification of a site activated during the 20–80%, preferably 35–50%, of the electrical diastolic period as referenced to the body surface electrocardiogram.

According to one embodiment of the present invention, there is provided a process for identification of an active site of diastolic activation during ventricular tachycardia including the steps of monitoring an ECG signal, monitoring the local diastolic activation time in relation to the ECG signal, mapping heart tissue in a chamber of the heart for an active site, and identifying the active site in the 20–80%, preferably 35–50%, time period of the diastolic interval and initiating the delivery of ablation energy to the active site. There may be more than one active site.

The system includes two parts. The first part includes the electrical activation data generation means, whether from a hand-held mapping probe or computerized electrode array in the operating room, or with an electrode catheter by percutaneous approach. The second part includes an interface with the ablation energy source. The first part guides the delivery of the ablation energy. This differs from old procedures in that the two functions have now been integrated into a system. The new aspect of the system includes a new recognition of the appropriate electrical markers of the active site of ventricular tachycardia coupled to an automated ablation delivery system. The problems solved by this invention include overcoming the unreliability of visually directed ablation with separately obtained sites of local activation. This is particularly important since the critical areas requiring ablation energy may require a reproducibility of location within 0.5 centimeters or less. For ventricular tachycardia, the critical ablation of the active site defined in electrical activation terms encompasses a critical window of electrical activation time within electrical diastole as viewed from the surface ECG, i.e., 20–80%, preferably 35–50%, of the time between QRS complexes of the arrhythmia. This critical window of activation timing has not previously been defined or has this activation time been coupled to the ablation source.

One significant aspect and feature of the present invention is the recognition that active sites occur during the 20–80%, preferably 35–50%, time period of a diastolic interval. With this recognition, the appropriate ablation of the active site can then be undertaken to eliminate the cells causing the VT condition as the ablation energy can automatically be delivered through the mapping device, or in the alternative, a second device adjacent to the mapping device.

Other significant aspects and features include that potentially dangerous energy cannot be delivered to normal heart muscle; therapeutic ablation energy can be delivered in spite of the transient nature of the arrhythmia; and the device overcomes serious problems imposed by movement of the mapping device while a physician is trying to visually access the activation time and make an independent judgment about energy delivery.

Another significant aspect and feature of the present invention is the recognition of a time zone of 160-50 milliseconds before the onset of a QRS complex in which active sites occur during VT.

A further significant aspect and feature of the present invention is that a site of origin for VT is now recognized as the active site.

Having thus described the embodiments of the present invention, it is a principal object hereof to provide a process for identification of an active site or sites for later ablation of the cells at the active site through the delivery of ablation energy.

Objects of the present invention include knowledge of the active site of the ventricular tachycardia; the knowledge of ablation effectiveness; and the coupling of the activation time to the energy ablation source.

Another object of the present invention provides an ablation system which is automatic in that when an active site is sensed by the ECG signal processing for a preferred 35-50% window in a 20-80% interval of the diastolic interval, energy is automatically switched to the energy delivery structure s that the electrophysiologist is not distracted during a mapping procedures. This automatic switching of energy enhances accurate delivery of energy to the mapped active site in a relatively instantaneous time period.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
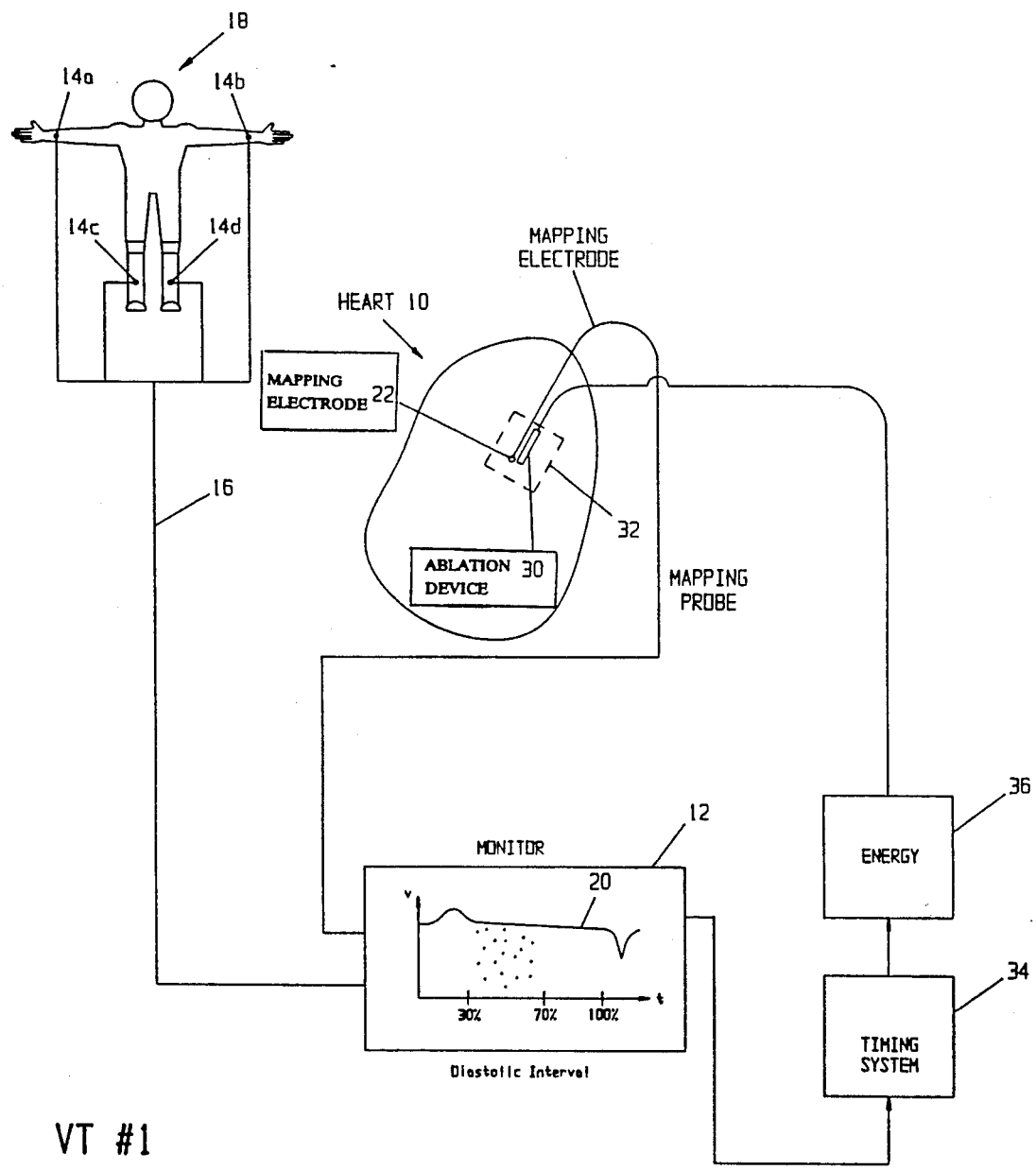
FIG. 1 illustrates a system schematic of a process for identification of an active site, as well as ablation of the active site.

FIG. 1 illustrates a system schematic of a process for identification of an active site including a heart of a patient 18, a monitor 12, and ECG electrodes 14a-14d connected by a cable 16 from the patient 18 to the monitor 12. A mapping electrode 22 for mapping of an active site or sites also connects to the monitor 12. A display 20 is shown on the monitor 12. A diastolic interval is obtained from the ECG signal between the QRS complexes.

A timing system 34 connects to the monitor 12 to switch a laser or other energy source 36 during sensing of an active site during the 20-80%, preferably 35-50%, time period of the diastolic interval and power an ablation device 30 with laser or other energy source for ablation of the VT cells at the active site. Other energy sources can include RF, microwave or DC energy to ablate the active site. The mapping electrode can also be used to deliver the RF, microwave or DC energy in lieu of using a separate ablation lead such as which would be required for delivery of laser energy. The ablation device 30 and mapping electrode 22 can position in the same housing such as at the end of a catheter. The mapping electrode 22 and the ablation lead 30 can be one in the same.

It is within the teachings of this disclosure that the mapping and the energy delivery structure for ablation of the heart tissue can be the same device, such as a catheter by way of example and for purposes of illustration only, and not to be construed as limiting of the present invention. As an example, the mapping electrode could be used to deliver the RF, microwave or DC energy. The laser delivery structure, such as a fiber optic and lens, could be arranged adjacent to the mapping electrodes or surrounded by the mapping electrodes in an appropriate catheter structure.

It is preferred that the mapping electrode and the ablation device are within the same structure such as a catheter as indicated by a box 32 in dashed lines.

MODE OF OPERATION

The steps of the process of identification of an active site for VT are performed by appropriate medical personnel in accordance with the Description of the Preferred Embodiments. The recognition of the active sites in the preferred 35-50% window, or broadly, the 20-80% window, of the diastolic, is the substance of the present invention.

In particular, each heart beat is displayed on monitor 12. A number of consecutive beats is monitored to verify the stability of the electrical recording. After the passage of one interval for which the time period is measured, a second interval begins and the appropriate window is taken. The catheter is put in place and the signal generated indicates whether it is in the window or not. If in the window, activation of ablation energy is initiated. If not in the window, the device is moved until in the window.

Various modifications can be made to the present invention without departing from the apparent scope hereof.

We claim:

1. Process for identification of sites of diastolic activation during ventricular tachycardia (VT) comprising the steps of:
    a. monitoring an ECG signal of a heart;
    b. measuring the time period of a diastolic interval of a heart in relation to said monitored ECG signal;
    c. determining the 20-80% time period of said measured diastolic interval;
    d. mapping heart tissue for an active site in said 20-80% time period; and,
    e. identifying the active site in said 20-80% time period.

2. Process of claim 1 further comprising:
    a. determining the 35-50% time period of said measured diastolic interval, mapping heart tissue for an active side in said 35-50% time period; and,
    b. identifying the active site in said 35-50% time period.

3. Process for identification of ablation of an active site comprising the steps of:
    a. monitoring an ECG signal of a heart;
    b. measuring the time period of a diastolic interval of a heart in relation to said monitored ECG signal;

c. determining the 20% to 80% time period of said measured diastolic interval;
d. mapping heart tissue for an active site with a mapping electrode;
e. identifying the active site in the 20-80% time period of said measuring time period of said diastolic interval; and,
f. switching an energy source to power an ablation means adjacent said mapping electrode to ablate the active site.

4. A system for location and ablation of an active site of ventricular tachycardia comprising:
a. a catheter;
b. a mapping electrode at one end of said catheter and connected to a signal processing and display generation means;
c. an ablation means at said end of said catheter;
d. said signal processing and display generation means connected to ECG signal generation means for processing and displaying the 20-80% time range of a diastolic interval;
e. an energy source connected to said ablation means; and,
f. a switch means connected between said signal processing and display generation means and said energy source to supply energy to said ablation means during 20-80% of a diastolic interval.

5. A system of claim 4 wherein said ablation means is a laser.

6. A system of claim 4 wherein said energy source is DC energy.

7. A system of claim 4 wherein:
a. said generation means processes and displays the 35-50% time range of a diastolic interval; and,
b. wherein said switch means supplies energy to ablation means during 35-50% of a diastolic interval.

8. A system of claim 4 wherein said energy source comprises a laser, and said mapping electrode and said ablation means including a laser optic means are in said catheter.

* * * * *

UNITED STATES PATENT AND TRADEMARK OFFICE
CERTIFICATE OF CORRECTION

PATENT NO. : 5,172,699
DATED : December 22, 1992
INVENTOR(S) : Robert H. Svenson and Wendell King It is certified that error appears in the above-indentified patent and that said Letters Patent is hereby corrected as shown below:

Column 4, line 61, claim 2, "side" should be --site--.

Column 3, line 31, "s" should be --so--.

Column 3, line 53, after "heart" insert --10--.

Signed and Sealed this

Twenty-sixth Day of July, 1994

Attest:

BRUCE LEHMAN

*Attesting Officer*  *Commissioner of Patents and Trademarks*